United States Patent [19]

Valkirs et al.

[11] Patent Number: 4,632,901
[45] Date of Patent: Dec. 30, 1986

[54] METHOD AND APPARATUS FOR IMMUNOASSAYS

[75] Inventors: Gunars E. Valkirs, San Marcos; Newton C. Owen, Encinitas; Philip A. Levinson, San Diego, all of Calif.

[73] Assignee: Hybritech Incorporated, San Diego, Calif.

[21] Appl. No.: 609,395

[22] Filed: May 11, 1984

[51] Int. Cl.⁴ .................... G01N 33/53; G01N 33/543
[52] U.S. Cl. ......................................... 435/5; 422/56; 422/57; 422/58; 435/7; 435/21; 435/287; 435/805; 436/513; 436/518; 436/548; 436/807; 436/818; 436/820; 436/824
[58] Field of Search ............ 435/5, 7, 287, 805, 435/21; 436/513, 527, 531, 548, 807, 808, 824, 810; 422/56–58

[56] References Cited

U.S. PATENT DOCUMENTS

| | | | |
|---|---|---|---|
| 3,615,222 | 10/1971 | Mead | 23/230 |
| 3,645,687 | 2/1972 | Nerenberg | 436/807 X |
| 3,715,192 | 2/1973 | Wenz et al. | 23/253 TP |
| 3,811,840 | 5/1974 | Bauer et al. | 23/230 TP |
| 3,825,410 | 7/1974 | Bagshawe | 23/230 R |
| 3,843,324 | 10/1974 | Edelman | 436/529 X |
| 3,888,629 | 6/1975 | Bagshawe | 23/230 B |
| 3,966,897 | 6/1976 | Renn et al. | 424/1.5 |
| 4,039,652 | 8/1977 | Adams et al. | 425/1 |
| 4,053,284 | 10/1977 | Posch | 23/259 |
| 4,061,468 | 12/1977 | Lange et al. | 23/253 TP |
| 4,094,647 | 6/1978 | Deutsch | 23/253 TP |
| 4,125,372 | 11/1978 | Kawai | 422/57 X |
| 4,138,474 | 2/1979 | Updike | 424/1 |
| 4,153,675 | 5/1979 | Kleinerman | 424/8 |
| 4,168,146 | 9/1979 | Grubb et al. | 23/230 B |
| 4,180,383 | 12/1979 | Johnson | 436/807 X |
| 4,193,983 | 3/1980 | Ullman et al. | 424/12 |
| 4,200,690 | 4/1980 | Root et al. | 435/7 |
| 4,235,601 | 11/1980 | Deutsch | 23/230 R |
| 4,246,339 | 1/1981 | Cole | 436/808 X |
| 4,305,924 | 12/1981 | Piasio et al. | 425/1 |
| 4,366,241 | 12/1982 | Tom et al. | 435/7 |
| 4,376,110 | 3/1983 | David | 436/808 X |
| 4,391,904 | 7/1983 | Litman et al. | 435/7 |
| 4,424,279 | 1/1984 | Bohn | 436/808 |
| 4,425,438 | 1/1984 | Bauman | 436/824 X |
| 4,427,769 | 1/1984 | Adlercreutz | 436/810 X |

Primary Examiner—Sidney Marantz
Attorney, Agent, or Firm—William L. Respess

[57] ABSTRACT

Disclosed herein is an apparatus and process for conducting immunoassays. The apparatus comprises a first member which is a membrane or a filter to which is bound an antibody, typically a monoclonal antibody, or which is capable of extracting cells from a fluid sample. The apparatus further comprises a second member which is composed of absorbent material which acts when in contact with the first member to induce flow through the first member when a fluid sample is added to it. The apparatus is used to conduct immunoassays by applying a sample to the upper surface of the first member to bind antigen in the sample by means of antibody fixed to the first member or, in certain cases, by extracting cellular material which has antigen associated with it. Addition of the sample is followed by addition of labeled antibody against the antigen being assayed followed by a washing step to remove unbound labeled antibody. The presence of labeled antibody on the first member after washing is indicative of the presence of the antigen in the sample being assayed.

16 Claims, 2 Drawing Figures

METHOD AND APPARATUS FOR IMMUNOASSAYS

FIELD OF THE INVENTION

This invention relates to immunoassay processes, particularly those using monoclonal antibodies. In another aspect it relates to an apparatus for conducting such immunoassays.

BACKGROUND

For nearly two decades, immunoassay procedures have provided sensitive diagnostic tools for the in vitro detection of a variety of antigens associated with disease or other physical conditions of clinical significance. Originally such heterogeneous assays used a polyclonal antibody preparation bound to the solid phase. In these assays, a solution of labeled antigen is allowed to compete with antigen in the sample being analyzed for the solid phase antibody. The extent to which the labeled antigen is bound to the solid phase or is detected in the liquid phase can be used as a measure of the presence and quantity of antigen in the sample being analyzed.

Subsequently, non-competitive immunometric assays became available. In these assays, a polyclonal antibody preparation bound to a solid phase was also used. The sample containing the suspected antigen was allowed to contact the solid phase in order for the antigen to bind to the antibodies on the solid phase. Typically, after an incubation step the sample was separated from the solid phase which was then washed and incubated with a solution of additional polyclonal antibodies which had been labeled, for example with a radionuclide, an enzyme, or a fluorescent moiety.

After this second incubation, the unbound labeled antibody was separated from the solid phase and the amount of labeled antibody in either the liquid phase or bound to the solid phase in an antibody:antigen:antibody sandwich was determined as a measure of the presence and/or concentration of antigen in the sample tested.

More recently, immunoassay procedures have been modified to use monoclonal antibodies. For example, U.S. Pat. No. 4,376,110 describes two-site immunometric assays using pairs of monoclonal antibodies, one bound to a solid phase and the other labeled to permit detection. The use of monoclonal antibody pairs which recognize different epitopic sites on an antigen has made it possible to conduct simultaneous immunometric assays in which the antigen and labeled antibody incubations do not require the intermediate washing steps of prior processes.

In the foregoing processes, the solid phase antibody is typically bound to a bead or small particles or coated on a surface. All of these processes characteristically require an incubation period with both the solid phase and labeled antibodies and, as a result, are time consuming even if conducted simultaneously. In fact, it is not unusual for an assay procedure to require several hours to complete. Furthermore, the need to adhere to timed incubation steps and plural washings with measured reagents has largely limited these procedures to large hospital and reference clinical laboratories where highly trained personnel and sophisticated equipment are available to perform the assays. As a result, there has gone unmet a need for a simple and rapid procedure for conducting immunoassays which employ a relatively simple apparatus to make such assays available for use in the physician's office and even for over-the-counter sale to laypersons for use in home health care programs.

SUMMARY OF THE INVENTION

The present invention provides a process for simply and rapidly performing immunoassays which uses a simple apparatus and which does not require lengthy incubation steps. The apparatus of the invention comprises, as a first member, a porous member such as a membrane or filter to which is bound antibody, preferably a monoclonal antibody against the target antigen, or which is capable of separating from the sample being analyzed cells or cellular debris with which the antigen being assayed is associated to thereby fix the antigen to the porous membrane. The apparatus further comprises, as a second member, an absorbent member having capillary pathways therethrough generally transverse to its upper and lower surfaces. As used herein, the term "capillary" includes a capillary or other channel or pathway which permits a liquid to traverse the absorbent member. The second member is in capillary communication with the porous first member and is selected to have a capillary pore size so as to induce flow of liquid through the first member without the use of external means when the hydrostatic pressure of the sample and subsequent addends used in the assay are not sufficient to induce flow through the first member. The second member may also provide support for the first member.

The assay of the present invention comprises the steps of adding a liquid sample to the porous member whereby, as the liquid flows through the member, antibody bound to the member binds antigen in the sample at a rate that is substantially faster than the rate observed in the absence of flow through the member. If the antigen is on the surface of cellular material, the cellular material is either bound by antibody bound to the member or is entrapped by the member as the sample flows through. The addition of sample is followed by addition of an antibody solution, preferably a solution of a monoclonal antibody, in which the antibody is labeled to permit detection. The preferred label is an enzyme although other labels, for example, a radionuclide or a fluorescent label may also be used. The antibody binds to the antigen previously extracted from the sample, either by the bound antibody or by entrapment of cellular material. The addition of labeled antibody may be followed immediately, or after a brief incubation to increase sensitivity by permitting greater binding of antigen and labeled antibody, by a washing step to remove unbound labeled antibody. The presence of labeled antibody on the porous member is then determined as an indication of the presence of the target antigen in the sample. In the case of an enzyme label this is done by addition of a solution of a color forming substrate to the member which reacts with the enzyme as the solution passes through it.

DESCRIPTION OF PREFERRED EMBODIMENTS

As noted above, the apparatus of the present invention comprises, as a first member, a porous membrane or filter to which is bound antibody or which is capable of filtering cellular material from a sample being assayed if the antigen is associated with the cellular material. In the latter case, the membrane or filter is selected to have a pore size which permits this separation. Any of a variety of filtering members may be used including glass fiber filters and filters of various synthetic or natural materials.

In a preferred embodiment the first member is a membrane or filter to which an antibody preparation is covalently bound. Preferably the antibody preparation comprises a monoclonal antibody even though polyclonal antibodies from antisera may be used. Techniques for polyclonal and monoclonal antibody preparation are now well known and require no citation here. The material of the member is selected from a material to which the antibody can be bound. A preferred material is nylon which has amino group residues or into which such groups have been introduced by chemical means, which permit antibodies to be coupled to it by the well known glutaraldehyde method. Antibodies can be coupled to glass fibers through aminosilanes. Other natural or synthetic materials which can be coupled directly or through intermediates to an antibody may also be used.

The second member is an absorbent member having capillary passageways generally transverse to the upper and lower surfaces. The second member is assembled with the first in a manner which permits direct communication between the pores or interstices of the first member and the capillaries of the second. Thus, as a liquid is applied to the first member and saturates it, the liquid is drawn into the absorbent member. As a result, flow can be induced through the first member when a liquid sample is applied to the upper surface of the first member even though the hydrostatic pressure of the fluid is so low that unaided it could not flow through the first member without the application of pressure to force it through or a vacuum to draw it through.

The selection of material for the second member is not critical and a variety of fibrous filter materials can be used. A useful material is cellulose acetate fibers oriented as in a cigarette filter. Those skilled in the art will appreciate that other absorbent members made of polyester, polyolefin or other materials may be used in place of cellulose acetate.

Figure 1:
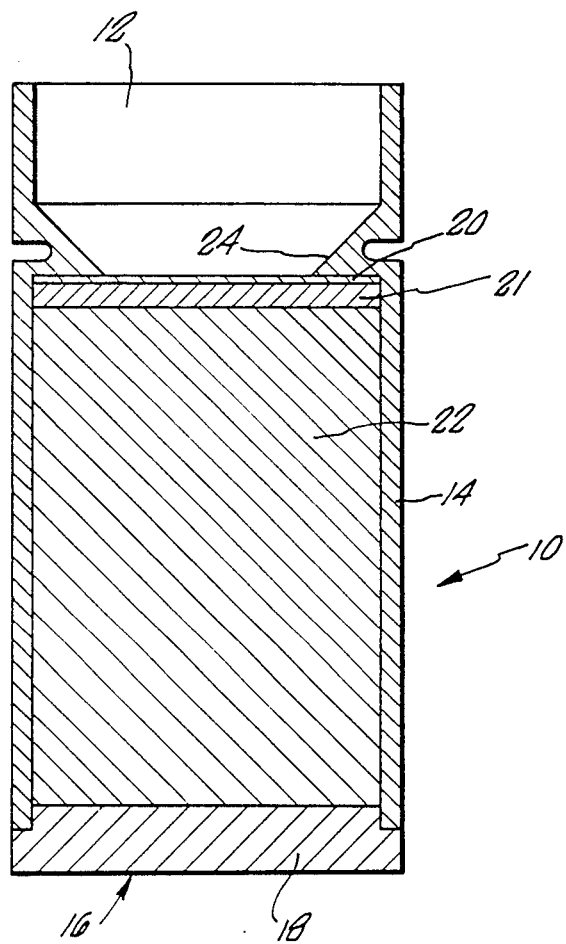
FIG. 1 is a cross-section of an apparatus for performing an immunoassay in accordance with the present invention.

Turning now to FIG. 1, there is shown in cross-section a device which can be used with the apparatus of this invention to perform immunoassays. Thus, in FIG. 1, a cylindrical container 10 although it may have any other appropriate shape is provided having an upper opening 12 defined by sidewall 14. The container may be made of glass or a suitable plastic material. As shown in FIG. 1, container 10 also has a lower opening 16, in which is inserted a removable plug 18, to permit insertion of the porous member 20, a circular membrane or filter disc, and an optional member 21, whose function is described below, which rest on cylindrical absorbent member 22, which is also inserted through opening 16.

A portion of container 10 is constricted as shown in FIG. 1 by reference numeral 24 to provide an integral funnel to direct sample onto the member 20 and to assure that effective washing of sample and other addends onto the member 20 is accomplished.

The size of member 22 and, therefore, the volume of the portion of container 10 below the constriction is preferably selected so that all of the liquid to be added to the apparatus during an assay can be received in and retained in absorbent member 22. Means for venting air (not shown in FIG. 1), for example, small ports, is provided in container 10, near the bottom, to allow displaced air to escape. Optionally, the bottom of container 10 can be eliminated and liquid allowed to pass through members 20 and 22 and exit the container through the bottom. However, since the article is intended to be disposable and to facilitate the disposal of sample in a simple and hygienic fashion, it is preferred to use a structure shown in FIG. 1.

As previously noted, member 20 may be used to either filter cellular material from a sample or as a support for bound antibody against the antigen being assayed. In either case, the liquid sample is applied to the member 20 by introduction through opening 12. After it permeates the member 20 and the liquid is drawn therethrough by and into absorbent member 22, a solution of labeled antibody, preferably a monoclonal antibody, is added through opening 12 to member 20.

The labeled antibody then binds either to antigen bound to antibody on the member 20 or associated with cellular material trapped on the surface of 20. If member 20 has a monoclonal antibody bound to it, and the labeled antibody is also a monoclonal antibody, the two antibodies are selected to bind to non-interfering antigen binding sites as described in U.S. Pat. No. 4,376,110 and application Ser. No. 323,498 filed June 6, 1981, the disclosures of which are incorporated by reference.

Preferably the soluble antibody is labeled with an enzyme although other conventional immunoassay labels may be used in appropriate circumstances. For example, a fluorescent label or a radionuclide can be used.

After the labeled antibody solution has passed through the member 20, a washing liquid is applied to member 20 to flush unbound labeled antibody from member 20 and into member 22. The sloping structure of the walls 24 provides an integral funnel to facilitate application of the washing liquid to the walls to remove adhered residue of the labeled antibody solution.

The addition of labeled antibody solution and washing liquid to the member 20 may be preceded by brief incubation periods to permit more extensive binding by antibody or antigen in solutions trapped on or in the interstices of member 20 and, thereby, increase the sensitivity of the assay. We have found, however, that such incubation steps are either unnecessary or may be very brief, i.e., on the order of 60 seconds or less. The flow of solutions containing antigen or labeled antibody through the member 20 results in a substantially faster rate of binding than is observed in the absence of flow.

If the antibody label is an enzyme, after washing to remove unbound antibody from member 20, a solution of the enzyme substrate is added to member 20. If the target antigen is bound either to antibody bound to member 20 or to cellular material on member 20, the antigen will have bound to it a portion of labeled antibody. The enzyme will cause the substrate to react and generate, if properly selected, a visual color change.

We have found that the use of cellulose acetate material for the absorbent member 22 may bind labeled antibody non-specifically at its upper surface. Accordingly, some visual color change may occur at this surface just under the member 20. To avoid this color change being visualized through member 20, a separating member (designated 21 in FIG. 1) of porous polyethylene or other material which does not bind antibody nonspecifically is preferably disposed between members 20 and 22.

Figure 2:
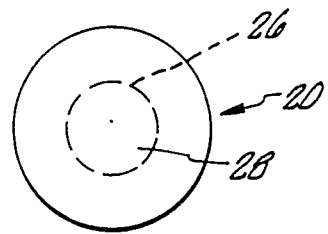
FIG. 2 is a top view of a porous member used in the invention for removing antigen from a sample being assayed.

Turning now to FIG. 2, there is shown a top view of member 20. The phantom line 26 represents the outer circumference of the area 28 in which antibody, preferably a monoclonal antibody, is bound in a preferred embodiment. This area has a diameter less than the diameter of the restriction formed by walls 24 at its narrowest point. Thus, when an enzyme is used as the antibody label the following results may occur: (1) the development of more color in the area 28 than in the periphery of member 20 will be read as a positive result; (2) if no color development is observed in member 20, a negative result is read; (3) if after washing some labeled antibody remains in the member 20, a modest color change which is uniform over the entire visible surface may occur. Such result is also interpreted as negative.

The foregoing is a general description of the apparatus and process of the invention. We have found it useful in performing immunoassays from introduction of sample to reading a positive result in less than five minutes. Thus, in a specific example, a monoclonal antibody against human choriogonadotropin (HCG), an antigen which is elevated in the urine of pregnant women, is bound to a porous nylon membrane using the glutaraldehyde technique and placed in a container such as 10 in FIG. 1 and supported there by an absorbent member of cellulose acetate but separated therefrom by a disc of porous polyethylene.

Samples of urine (4 ml containing 0 and 50 mIU/ml of HCG) were added to the apparatus described and drawn through members 20 and 21 into the absorbent material 22. Three (3) drops of a solution of second monoclonal antibody against HCG to which is bound alkaline phosphatase were then added. After a brief incubation, about 1 minute, during which time the conjugate is drawn through member 20, 4 ml of water was added to remove unbound antibody from member 20. This addition was followed by three drops of a solution containing indoxyl phosphate, a substrate for alkaline phosphatase. After two minutes no color developed in the device used to test the sample containing no HCG (0 mIU/ml). For the 50 mIU/ml HCG sample a distinct blue color developed in the center of the disc within thirty seconds which became dark blue within two minutes. No color developed in the periphery of the disc. The entire assay consumed about five (5) minutes. It will be appreciated that the sensitivity of the assay may be adjusted by varying the volume or incubation times.

Although the invention has been described using an assay for HCG as an example, it will be appreciated that a similar assay for other antigens may be constructed. The entire list of target antigens is too lengthy to be listed, but antigens such as IgE, prostatic acid phosphatase, prostate specific antigen, alphafetoprotein, carcinoembryonic antigen, leutenizing hormone, creatine kinase MB and other antigens in serum, plasma, urine, or other liquid media may be detected. Additionally, liquid samples containing material having antigens associated therewith such as antigens associated with bacteria, parasites, fungi, or viruses including, for example, group A and B streptococcus, *Neisseria gonorrhea, Gardnerella vaginalis, Trichomonas vaginalis, Candida albicans, Chlamydia trachomatis,* hepatitis B, and cytomegalovirus can be detected by using a filter which will trap the cells or a filter to which antibody specific for the antigen is bound as member 20. Addition of a solution of a monoclonal antibody labeled, for example, with an enzyme, will result in binding of the antibody to the antigen. Washing and substrate addition will result in the color change associated with presence of the labeled antibody on the cells, which can be detected visually or by aid of an instrument.

If a label other than an enzyme is used, the procedure may be varied. Fluorescence of the membrane could be measured if a fluorescing label is used. If a radionuclide label such as $^{125}I$ is used, the membrane can be removed and counted. These and other variations may be made by persons skilled in the art without departure from the spirit of the invention.

We claim:

1. An apparatus for use in an immunoassay process for the detection of a target antigen in a liquid sample comprising:
   (a) a first member which is a porous membrane or filter and to which is bound an antibody against the target antigen, which member has upper and lower surface, the sample being applied to the upper surface, and wherein the antibody is bound within an area smaller than the area of the member to which the sample is applied; and
   (b) a second member which is a body of absorbent material having a surface over which the first member is placed and having capillaries therethrough in a direction generally transverse to the surface over which the first member is placed, which capillaries are in communication with the pores on the lower surface of the first member so as to draw liquid added to the upper surface which has permeated the first member into the capillaries of the member, the capillary communication between said first and second members having been established prior to, and maintained during, addition of liquids to the apparatus in the immunoassay process.

2. An apparatus according to claim 1 wherein the antibody is a nomoclonal antibody.

3. An apparatus according to claim 1 wherein the membrane or filter is of glass or of nylon.

4. An apparatus according to claim 1 wherein the first member is separated from the second member by another porous member.

5. An apparatus according to claim 1, 2, 3, or 4 wherein the apparatus further comprises a container for the first and second members having an opening to permit addition of assay reagents to the upper surface of the first member.

6. An apparatus according to claim 5 wherein the opening further comprises a section having sides which slope inwardly to define a funnel for direction of the added reagents onto the upper surface of the first member.

7. An apparatus according to claim 5 wherein the bottom end of the container is closed, the container being vented to allow escape of displaced air.

8. An immunoassay process for the detection of a target antigen in a liquid sample employing as an assay device an apparatus comprising:
   (a) a first member which is a porous membrane or filter and to which is bound an antibody against the target antigen which member has upper and lower surfaces, the sample being applied to the upper surface, and wherein the antibody is bound within an area smaller than the area of the member to which the sample is applied; and (b) a second member which is a body of absorbent material having a surface over which the first member is placed and having capillaries therethrough in a direction generally transverse to the surface over which the first member is placed, which capillaries are in communication with the pores on the lower surface of the first member so as to draw liquid added to the upper surface which has permeated the first member into the capillaries of the second member, the capillary communication between said first and second member having been established prior to, and maintained during, addition of liquids to the apparatus in the immunoassay process;

the process comprising adding the sample and other reagents used in the assay to the upper surface of the first member and detecting antigen bound to the antibody on the first member.

9. A process according to claim 8 wherein the sample is added first followed by addition of labeled antibody to the target antigen.

10. A process according to claim 9 wherein addition of labeled antibody is followed by washing unbound labeled antibody from the first member followed by detection of the labeled antibody, if any, bound to the first porous member.

11. A process according to claim 10 wherein the labeled antibody is labeled with an enzyme and the washing step is followed by addition to the porous member of a substrate for the enzyme which enzyme and substrate are selected to generate a color change which is either visible of determined by instrumental means.

12. A process according to claim 8, 10 or 11 wherein the antigen is selected from human choriogonadotropin, IgE, prostatic acid phosphatase, prostate specific antigens, alphafetoprotein, carcinoembryonic antigen, leutenizing hormone, creatine kinase MB, or antigens associated with hepatitis B, cytomegalovirus, herpes, and *Chlamydia trachomatis*.

13. A process according to claim 12 wherein the sample is urine, serum, plasma, or other liquid media.

14. A process according to claim 9, 10 or 11 wherein the bound and labeled antibodies are monoclonal antibodies which bind, respectively, to non-interfering epitopes on the antigen.

15. A process according to claim 14 wherein the labeled antibody is labeled with an enzyme.

16. A process according to claim 15 wherein a solution of enzyme substrate is added after addition of the labeled antibody.

* * * * *